US008679005B2

(12) United States Patent
Gutierrez et al.

(10) Patent No.: US 8,679,005 B2
(45) Date of Patent: Mar. 25, 2014

(54) POSTERIOR TISSUE RETRACTOR FOR USE IN HIP REPLACEMENT SURGERY

(76) Inventors: Hialy Riviera Gutierrez, Staten Island, NY (US); Nicholas Giori, Stanford, CA (US)

( * ) Notice: Subject to any disclaimer, the term of this patent is extended or adjusted under 35 U.S.C. 154(b) by 1071 days.

(21) Appl. No.: 12/165,242

(22) Filed: Jun. 30, 2008

(65) Prior Publication Data

US 2009/0012370 A1    Jan. 8, 2009

Related U.S. Application Data

(60) Provisional application No. 60/937,533, filed on Jun. 28, 2007.

(51) Int. Cl.
*A61B 1/32* (2006.01)
(52) U.S. Cl.
USPC .......................................................... 600/201
(58) Field of Classification Search
USPC .................... 600/201–246; 606/96–97, 99
See application file for complete search history.

(56) References Cited

U.S. PATENT DOCUMENTS

| 4,610,243 | A | * | 9/1986 | Ray | ................................ | 600/206 |
| 5,303,694 | A |   | 4/1994 | Mikhail |  |  |
| 5,533,982 | A | * | 7/1996 | Rizk et al. | ...................... | 604/239 |
| 6,676,706 | B1 |  | 1/2004 | Mears et al. |  |  |
| 6,855,149 | B2 |  | 2/2005 | Dye |  |  |
| 7,172,554 | B2 |  | 2/2007 | Gustke et al. |  |  |
| 7,331,965 | B2 |  | 2/2008 | Nielsen |  |  |
| 2006/0189848 | A1 | * | 8/2006 | Penenberg | ...................... | 600/210 |
| 2006/0287584 | A1 | * | 12/2006 | Garcia-Bengochia | ........ | 600/213 |
| 2007/0260122 | A1 | * | 11/2007 | Murphy | ......................... | 600/201 |

OTHER PUBLICATIONS

ANT 211 Fundamentals of Forensic Anthropology, University of North Carolina Wilmington, [online] [retrieved on Feb. 27, 2008] URL: http://people.uncw.edu/albertm/ant211spring2008/Sex/sex.htm.
Cobra Retractors from Innomed, Inc., Orthopedics Product Details [online] [retrieved on Mar. 27, 2008] URL: http://www.medcompare.com/details/33014/Cobra-Retractors.html.
Innomed—New Instrument [online] [retrieved on Mar. 27, 2008] URL: http://www.innomed.net/new_products.htm.
Veterinary Instrumentation, Total Hip Replacement Kit, [online] [retrieved on Mar. 28, 2008] URL: http://k9ccl.com/product.php-?productid=23909&cat=8&page=1.

* cited by examiner

*Primary Examiner* — Heidi M Eide
(74) *Attorney, Agent, or Firm* — Brian S. Boyer; Syndicated Law, PC (57) ABSTRACT

A posterior retractor is provided, including a handle section; and, a retraction section having an anchoring element. The handle section has a proximal region, a mid-region, and a distal region. And, the length of the handle section can be sufficient to position a hand-held portion of the proximal region of the handle section outside of a surgical site during use of the posterior retractor in a hip arthroplasty procedure. A use of the posterior retractor in a hip arthroplasty procedure is described.

15 Claims, 8 Drawing Sheets

PRIOR ART

POSTERIOR TISSUE RETRACTOR FOR USE IN HIP REPLACEMENT SURGERY

CROSS-REFERENCE TO RELATED APPLICATIONS

This application claims the benefit of U.S. Provisional Application Ser. No. 60/937,533, filed Jun. 28, 2007, which is hereby incorporated herein by reference in its entirety.

BACKGROUND OF THE INVENTION

1. Field of the Invention

The teachings provided herein generally relate to a device and a method for performing a hip surgery that includes posterior retraction of soft tissue.

2. Description of the Related Art

More than 249,000 hip replacement surgeries are performed each year in the United States. Traditionally, hip surgeries required large incisions ranging from about 6 inches to about 12 inches in length, depending on the size of the patient and whether the surgery is a hip revision or a total hip arthroplasty, The larger the incision, the more risk there is to a number of important stabilizing muscles and tendons, potentially introducing further damage to the hip joint and surrounding soft tissue. Larger incisions also lead to larger blood losses, longer rehabilitation times, and larger scars. Minimally invasive surgery is now used and can reduce the incision to 3-5 inches. A patient can experience a faster recovery, and the hospital stay can often be reduced substantially, significantly lowering the cost of the hospital fees.

The instruments used in minimally invasive surgery should provide a surgeon with the ability to precisely locate the implant without complications, such as dislocation or subluxation, and should allow the surgeon to work within the relatively limited space of the smaller incision. The posterior retractor is commonly used in hip surgeries, such as the poster-inferior retractors available from Innomed, Inc., Savannah, Ga., 31404. See also, U.S. Pat. No. 6,855,149.

During a hip arthroplasty, the tissues posterior to the acetabulum are retracted, that is, pulled back away from the acetabulum using a standard "posterior retractor" to prepare the acetabulum for the insertion of a prosthesis. Problems associated with the use of currently available posterior retractors include the inability to reliably anchor the retractor and apply a stable leverage in the amount necessary to pull back the tissues. Currently available posterior retractors rely on a projection of bone (the "posterior lip") posterior to the acetabulum to anchor the retractor and provide this leverage. Unfortunately, in patients with bone disorders such as arthritis or osteoporosis, the posterior lip often does not provide optimal leverage or stability, given the deformation and corrosion of the affected area.

A reliable anchoring and stable leverage system would allow for more effective retraction of soft tissue, avoidance of the sciatic nerve, and optimal visualization of the acetabulum. Furthermore, currently available posterior retractors are used for only the left hip or the right hip. Accordingly, practitioners would appreciate a posterior retractor that provides reliable anchoring to the pelvic bone and the associated benefits of having stable leverage. Such an instrument would provide an effective and stable retracing of the posterior muscles surrounding the acetabulum, provide an adequate clearance in and around the surgical area, be useful in the arthroplasty of hips having common acetabular diameters, and be a simple and reliable device made from an FDA approved material that can be easily cleaned and sterilized. Moreover, an instrument having a design that could be used equally well with either the right or left hip would also add substantially to the appeal of the tool, reducing the need for multiple tools.

SUMMARY OF THE INVENTION

The teachings provided herein are generally directed to a posterior retractor comprising a handle section; and, a retraction section having an anchoring element. In most embodiments, the handle section comprises a proximal region, a mid-region, and a distal region. The length of the handle section is sufficient to position a hand-held portion of the proximal region of the handle section outside of a surgical site during use of the posterior retractor in a hip arthroplasty procedure.

In most embodiments, the retraction section has a proximal region and a distal region, wherein the proximal region of the retraction section joins the distal region of the handle, and the distal region of the retraction section has a pelvic surface. In these embodiments, the anchoring element can extend substantially normal to the pelvic surface of the retraction section, is fashioned for penetration of an ischial bone, and functions to anchor the retraction section of the posterior retractor to the subject's pelvis during use of the posterior retractor in the hip arthroplasty procedure.

In some embodiments, the posterior retractor comprises a handle section; and, a retraction section having an anchoring element; wherein, the handle section, the retraction section, and the anchoring element each have a central axis and are positioned relative to a horizontal plane. In these embodiments, the handle section can comprise a proximal region, a mid-region, and a distal region, wherein the mid-region has a planar cross-section that divides the mid-region equally along its length and is on the horizontal plane. The central axis of the mid-region can be at an angle ranging from about 90° to about 150° to the central axis of the retraction section, wherein the central axis of the retraction section can be at least substantially on a vertical plane that is normal to the horizontal plane. The handle section can have a length that is sufficient to position a hand-held portion of the proximal region of the handle section outside of a surgical site during use of the posterior retractor in a hip arthroplasty procedure.

In these embodiments, the retraction section can have a proximal region and a distal region, wherein the proximal region of the retraction section joins the distal region of the handle. The distal region of the retraction section has a pelvic surface that contacts a subject's pelvis during use of the posterior retractor. The retraction section can comprise a one-piece, rigid, semi-cylindrical shape having (i) a diameter of curvature that ranges from about 20 mm to about 90 mm and is at least substantially complementary to an acetabulum, and (ii) an arc ranging from about 45° to about 180°. The retraction section can have a concave surface facing away from the handle section and a convex surface facing toward the handle section.

In these embodiments, the anchoring element can extend substantially normal to the pelvic surface of the retraction section, is fashioned for penetration of an ischial bone, and can function to anchor the retraction section of the posterior retractor to the subject's pelvis during use of the posterior retractor in the hip arthroplasty procedure.

In some embodiments, the distal region of the handle can have a central axis that is normal to the central axis of the retraction section, of which neither central axis is on the horizontal plane, and can form an angle with the mid-region of the handle section such that the central axis of the mid-region can be at an angle ranging from about 30° to about 60° to the central axis of the retraction section. In some embodiments, the central axis of the mid-region is at an angle of 45° to the central axis of the retraction section.

In some embodiments, the distal region of the handle section has an impact surface for receiving a pressure that forces the anchoring element to penetrate the ischial bone. In some embodiments, the proximal region of the handle section is ergonomically curved away from the horizontal plane in a direction that opposes the direction in which the concave surface of the retraction section faces. In some embodiments, the handle section ranges in length from about 6 inches to about 12 inches. And, in some embodiments, the distance from the distal region of the handle section to the pelvic surface of the retraction section ranges from about 1 inch to about 3 inches. In some embodiments, the anchoring element ranges from about 0.25 inches to about 0.75 inches in length from the pelvic surface of the retraction section to the tip of the anchoring element.

The posterior retractor can comprise a surgical grade iron alloy having from about 12% to about 20% chromium, from about 0.2% to about 3% molybdenum, from about 8% to about 12% nickel and from about 0.08% to about 0.25% carbon. In some embodiments, the retractor can be fashioned from the surgical grade iron alloy as a single-piece instrument.

In some embodiments, the central axes of the handle section, the retraction section, and the anchoring element can all lie on the vertical plane. Moreover, in some embodiments, the retractor can have a shape that useful in the arthroplastic procedures of both the right hip and the left hip of the subject.

The teachings also include posterior retractor embodiments, wherein the retractor comprises a handle section; and a retraction section comprising an anchoring element; wherein, the handle section, the retraction section, and the anchoring element each have a central axis and are positioned relative to a horizontal plane. The handle section can comprise a proximal region, a mid-region, and a distal region, wherein the mid-region can be on the horizontal plane, and the central axis of the mid-region can be at an angle ranging from about 35° to about 50° to the central axis of the retraction section, which may not be on the horizontal plane.

In some embodiments, the handle section can have a length ranging from about 7 inches to about 9 inches, a width that is equal along the length of the handle section ranging from about 0.75 inches to about 2.0 inches, and a thickness that is 0.05 inches to about 0.25 inches. And, in these embodiments, the proximal region of the handle section can be ergonomically curved away from the horizontal plane and in the direction of the anchoring element.

In these embodiments, the retraction section can have a proximal region and a distal region, wherein the proximal region of the retraction section joins the distal region of the handle. And, the distal region of the retraction section can have a pelvic surface that contacts a subject's pelvis during use of the posterior retractor. The retraction section can comprise a one-piece, rigid, semi-cylindrical shape having (i) a diameter of curvature that ranges from about 20 mm to about 90 mm and is at least substantially complementary to an acetabulum, and (ii) an arc ranging from about 45° to about 180°. The retraction section can also have a concave surface facing away from the handle section and a convex surface facing toward the handle section.

In these embodiments, the distance from the distal region of the handle section to the pelvic surface of the retraction section can range from about 1 inch to about 2 inches, and the thickness of the retraction section ranges from about 0.05 inches to about 0.25 inches. Moreover, the distal region of the handle section has an impact surface for receiving a pressure that forces the anchoring element to penetrate an ischial bone.

In these embodiments, the anchoring element extends substantially normal to the pelvic surface of the retraction section, is fashioned for penetration of the ischial bone, ranges from about 0.25 inches to about 0.75 inches in length from the pelvic surface of the retraction section to the tip of the anchoring element, and functions to anchor the retraction section of the posterior retractor to the subject's pelvis during use of the posterior retractor in the hip arthroplasty procedure.

In some embodiments, the retractor is fashioned as a single-piece instrument from a surgical grade iron alloy comprising from about 12% to about 20% chromium, from about 0.2% to about 3% molybdenum, from about 8% to about 12% nickel and from about 0.08% to about 0.25% carbon. In some embodiments, the central axes of the handle section, the retraction section, and the anchoring element all lie at least substantially on the same vertical plane, which is at least substantially normal to the horizontal plane; and, in some embodiments, the retractor has a shape that useful in the arthroplastic procedures of both the right hip and the left hip of the subject;

In some embodiments, the teachings provide a posterior retractor, comprising a handle section having a means for (i) applying leverage to a retraction section and (ii) retracting soft tissue around a hip joint during an arthroplastic procedure. In these embodiments, the retraction section comprises a means for anchoring the posterior retractor a pelvic surface of a subject having the arthroplastic procedure. And, in these embodiments, the posterior retractor can comprise a surgical grade iron alloy comprising from about 12% to about 20% chromium, from about 0.2% to about 3% molybdenum, from about 8% to about 12% nickel and from about 0.08% to about 0.25% carbon. In some embodiments, the retractor can be fashioned from the surgical grade iron alloy as a single-piece instrument.

The teachings provided herein also include a method of implanting an acetabular prosthesis. The method comprises incising soft tissue over a hip joint comprising an acetabulum having a socket, and a femoral head. Any retractor taught herein is positioned posterior to the acetabulum such that the anchoring element is placed substantially normal to an ischial bone surface, and the concave surface of the retraction element is placed substantially complementary to the acetabulum. The anchoring element is forced into the ischial bone to anchor the retraction section to the ischial bone, and the soft tissue is retracted with the retracting section. The socket of the acetabulum is reamed to prepare the socket for insertion of an acetabular prosthesis; and, the acetabular prosthesis is positioned in the acetabulum. The teachings provided herein also include a kit comprising any of the retractors taught herein, a mallet for applying force to the anchoring element of the retractor; and, an acetabular reamer to prepare the socket of an acetabulum for insertion of an acetabular prosthesis. In some embodiments, the kits further comprise a femoral saw, a femoral reamer, and a femoral rasp. In some embodiments, the kits further comprise a set of acetabular reamers of a variety of sizes to prepare the socket of an acetabulum for insertion of an acetabular prosthesis.

DETAILED DESCRIPTION OF THE INVENTION

The teachings provided herein are generally directed to a posterior retractor comprising a handle section; and, a retraction section having an anchoring element. One of skill will appreciate that the true scope and applicability of the inventions provided herein is broader than the limited embodiments described by the teachings.

Figure 1A:
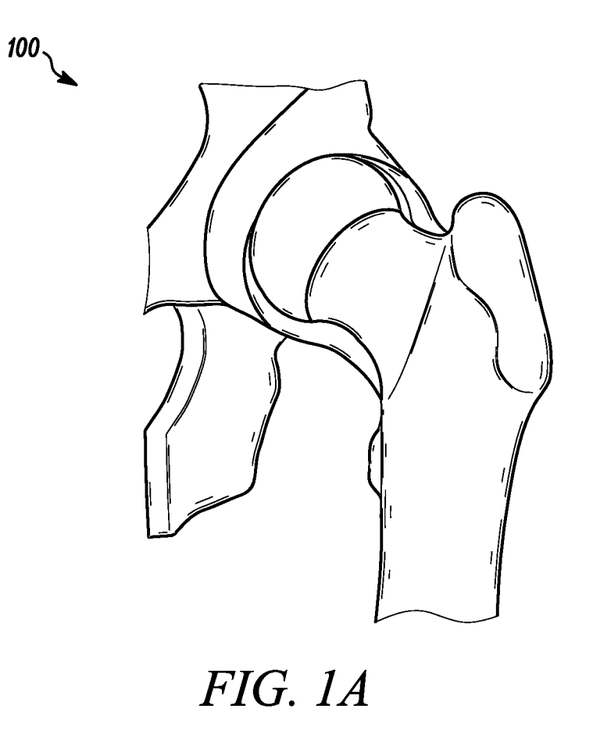
FIGS. 1a-1f illustrate basic steps of a hip surgery, according to some embodiments.
Figure 1B:
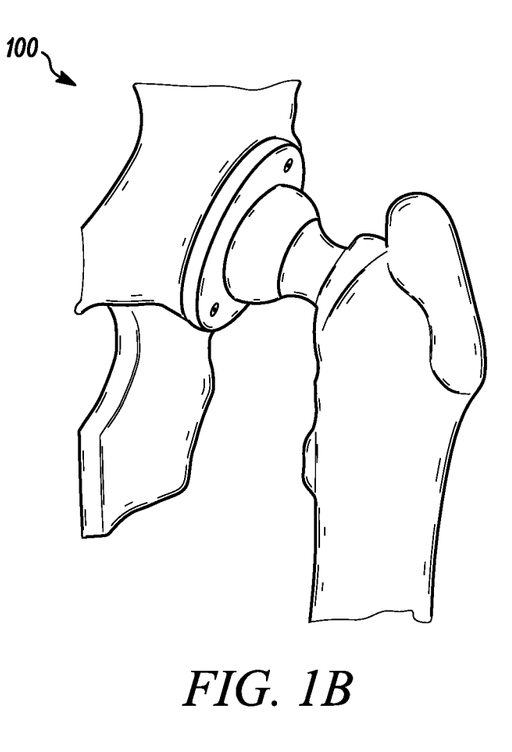
Figures 1C, 1D:
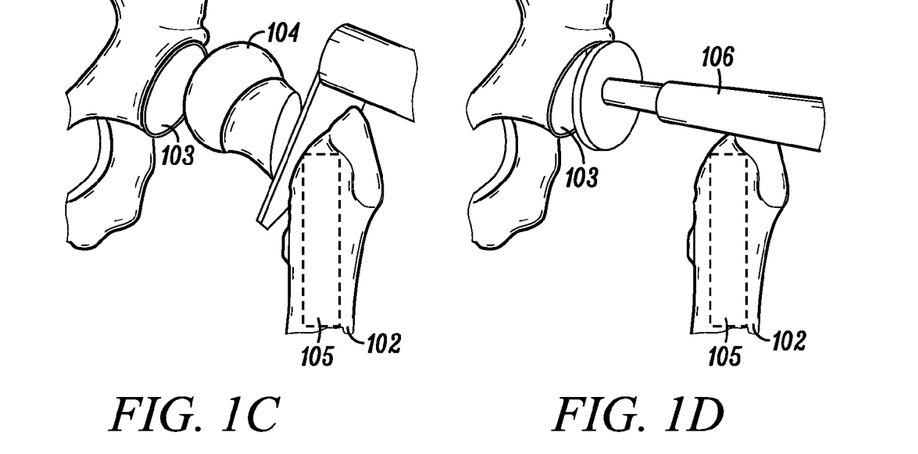
Figure 1E:
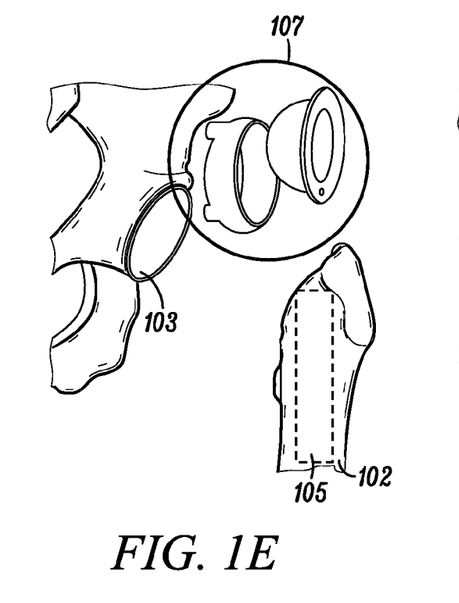
Figure 1F:
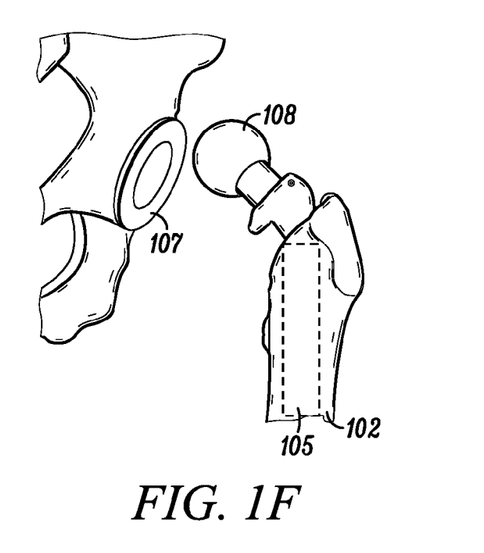

FIGS. 1a-1f illustrate basic steps of a hip surgery, according to some embodiments. FIG. 1a shows a hip 100 prior to the surgery, and FIG. 1b shows the hip 100 after arthroplasty. In FIG. 1c, the damaged femur is extracted from the acetabular socket 103 and the femoral head 104 is cut off. A tunnel 105 is then created in the femur 102 with a file. In FIG. 1d, the acetabular socket 103 is then prepared with a reamer 106 to smooth the socket 103 and prepare it for insertion of a prosthetic acetabulum 107 as shown in FIG. 1e. A prosthetic femoral head 108 is inserted into the tunnel 105 in the femur 102 and connected to the prosthetic acetabulum 107 as shown in FIG. 1f.

Figures 2A, 2B:
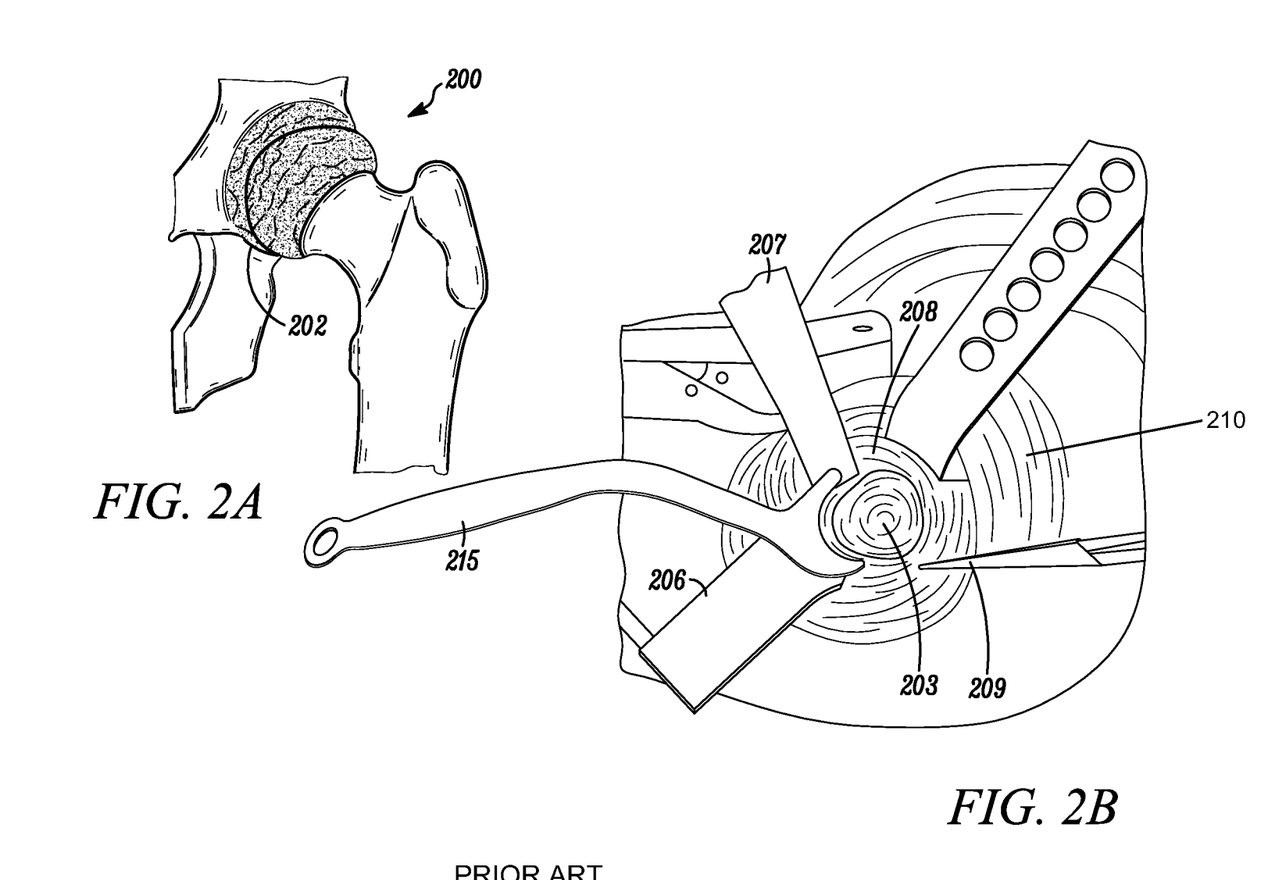
FIGS. 2a and 2b illustrate an anchoring problem with state-of-the-art retractors, according to some embodiments.

FIGS. 2a and 2b illustrate an anchoring problem with state-of-the-art retractors, according to some embodiments. In FIG. 2a, arthritic hip joint 200 has a degraded posterior lip 202 of an acetabulum 203. In FIG. 2b, retractors 206,207,208, and clamp 209, are used to pull back soft tissue 210 from the acetabulum 203. A poster-inferior retractor 215 is then used to provide clearance for a reamer 106 in the acetabulum 203 to prepare the acetabulum 203 for an arthroplasty.

The retractor 215 is leveraged by placing the retractor 215 under the posterior lip 202 and pressing the retractor 215 against the posterior lip 202 to retract tissue away from the acetabulum 203. The inability to leverage the retractor 215 and retract soft tissue can occur from a variety of conditions known to one of skill. As a result, an anchoring and stability problem produces inadequate leverage when pressing the retractor 215 against the posterior lip 215. The posterior lip 215 can be degraded from arthritis, such as in the case of the arthritic hip joint 200 or, the posterior lip 202 may simply have a shape that does not effectively hold the retractor 215 while applying leverage. The posterior lip 202 can also be weak and unable to sustain a leveraging force from retractor 215 due to a physiological disorder, such as osteoporosis. This current inability to leverage a stable retraction of the soft tissue around the hip joint creates a need for an improved posterior retractor.

Figure 3A:
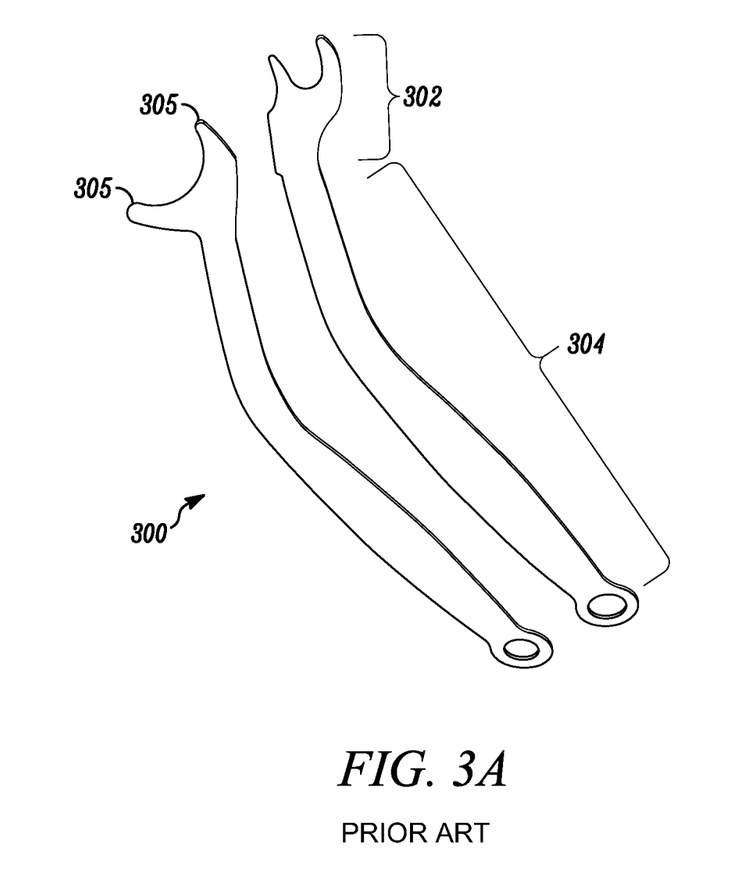
FIGS. 3a and 3b compares the state-of-the-art posterior-inferior retractors to a posterior retractor taught herein, according to some embodiments.
Figure 3B:
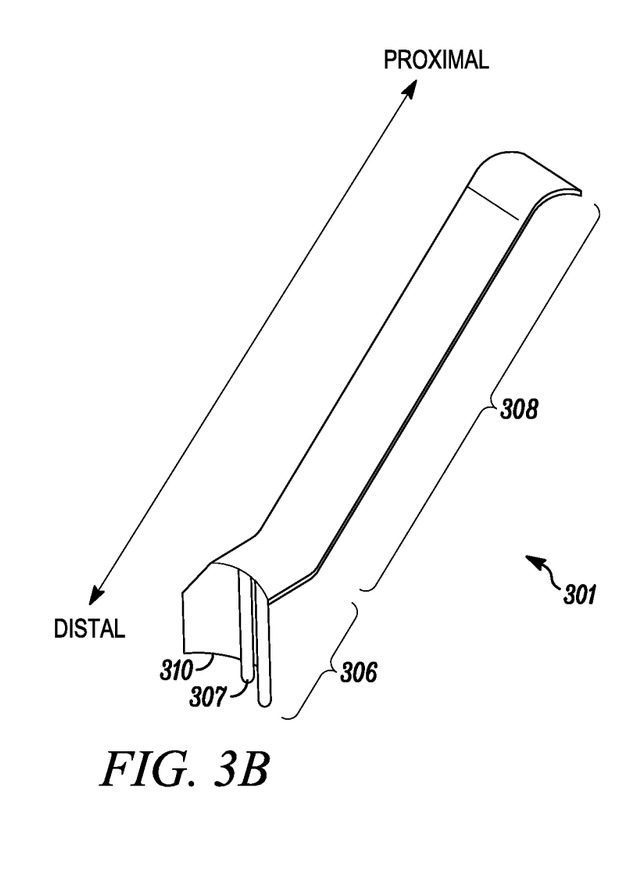

FIGS. 3a and 3b compares the state-of-the-art posterior-inferior retractors to a posterior retractor taught herein, according to some embodiments. In FIG. 3a, examples of right and left retractors 300 are shown. FIG. 3b illustrates a posterior retractor 301 taught herein. Each retractor 300 comprises a retractor section 302 and a handle section 304, wherein the retractor section 302 has prongs 305 that are used to obtain leverage against the posterior lip to pull back the soft tissue around a hip.

In FIG. 3b, the posterior retractor 301 has a handle section 308; and, a retraction section 306 having an anchoring element 307. In most embodiments, the handle section 308 comprises a proximal region, a mid-region, and a distal region. An arrow in the figures illustrates the meaning of "proximal" relative to "distal." And, the length of the handle section 308 is sufficient to position a hand-held portion of the proximal region of the handle section 308 outside of a surgical site during use of the retractor in a hip arthroplasty procedure. In most embodiments, the retraction section 306 has a proximal region and a distal region, wherein the proximal region of the retraction section 306 joins the distal region of the handle section 308, and the distal region of the retraction section 306 has a pelvic surface 310. In these embodiments, the anchoring element 307 can extend substantially normal to the pelvic surface 310 of the retraction section 306, is fashioned for penetration of an ischial bone, and functions to anchor the retraction section 306 of the posterior retractor 301 to the subject's pelvis during use of the posterior retractor 301 in the hip arthroplasty procedure.

Figure 4:
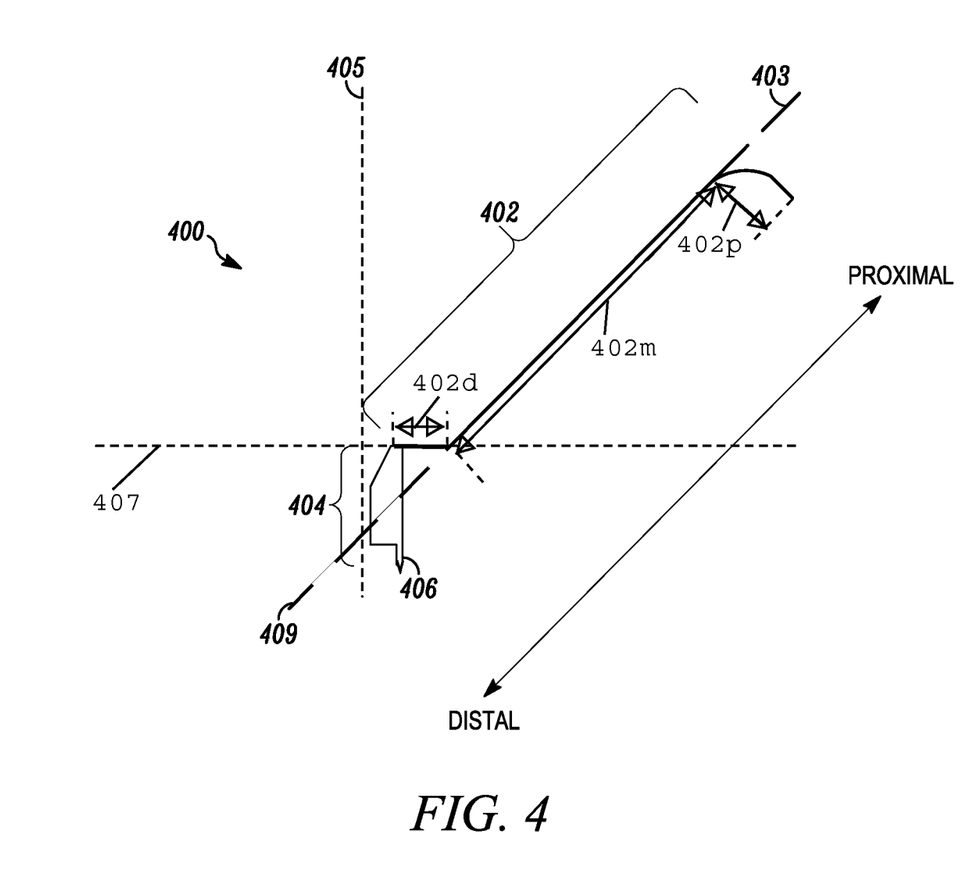
FIG. 4 illustrates a profile of a posterior retractor design, according to some embodiments.

FIG. 4 illustrates a profile of a posterior retractor design, according to some embodiments. In some embodiments, the posterior retractor 400 comprises a handle section 402; and, a retraction section 404 having an anchoring element 406; wherein, the handle section 402, the retraction section 404, and the anchoring element 406 each have a central axis 403, 405 and are positioned relative to a horizontal plane 409. In these embodiments, the handle section 402 can comprise a proximal region 402p, a mid-region 402m, and a distal region 402d, wherein the mid-region 402m has a planar cross-section that divides the mid-region equally along its length and is on the horizontal plane 409. The central axis 403 of the mid-region 402m can be at an angle ranging from about 90° to about 150° to the central axis 405 of the retraction section 404, wherein the central axis 405 of the retraction section 404 can be at least substantially on a vertical plane that is at least substantially normal to the horizontal plane 409. The central axis 407 of a distal region of the handle section 402 can be at least substantially on the vertical plane normal to the horizontal plane 409, wherein the central axis 407 can be at least substantially normal to the central axis 405 of the retraction section 404, in some embodiments. The handle section 402 can have a length that is sufficient to position a hand-held portion of the proximal region 402p of the handle section 402 outside of a surgical site during use of the posterior retractor 400 in a hip arthroplasty procedure. Again, an arrow in the figure illustrates the meaning of "proximal" relative to "distal."

The phrase "substantially" can refer to a variation, such as a variation in position, that is insubstantial, which means that the performance of the posterior retractor would not significantly differ by this amount of variation. For example, an axis that is at least substantially on a plane would indicate a variation in position of the axis that would produce a posterior retractor having nearly the same performance characteristics as a posterior retractor having the axis directly on the plane.

Figure 5A:
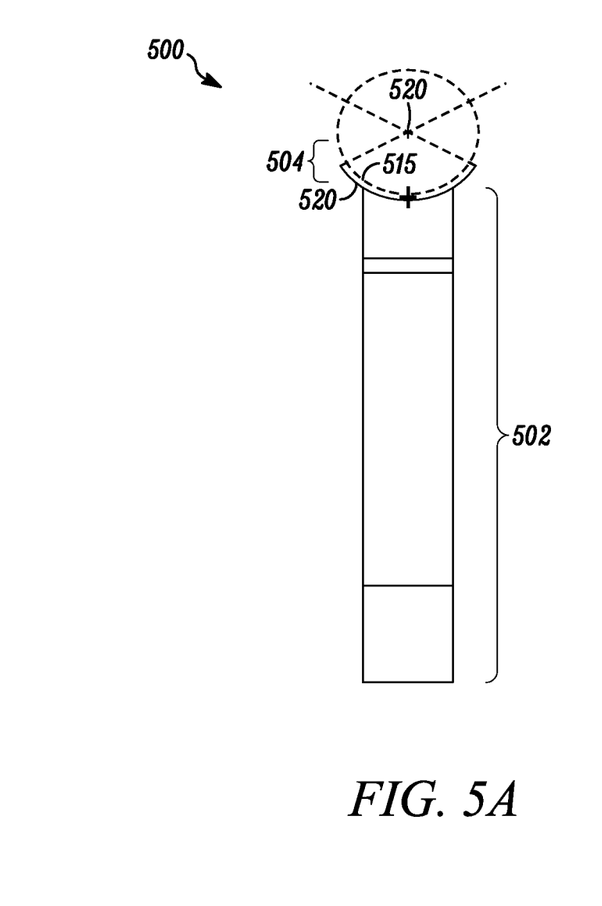
FIGS. 5a and 5b illustrate additional perspective views of a posterior retractor design, according to some embodiments.
Figure 5B:
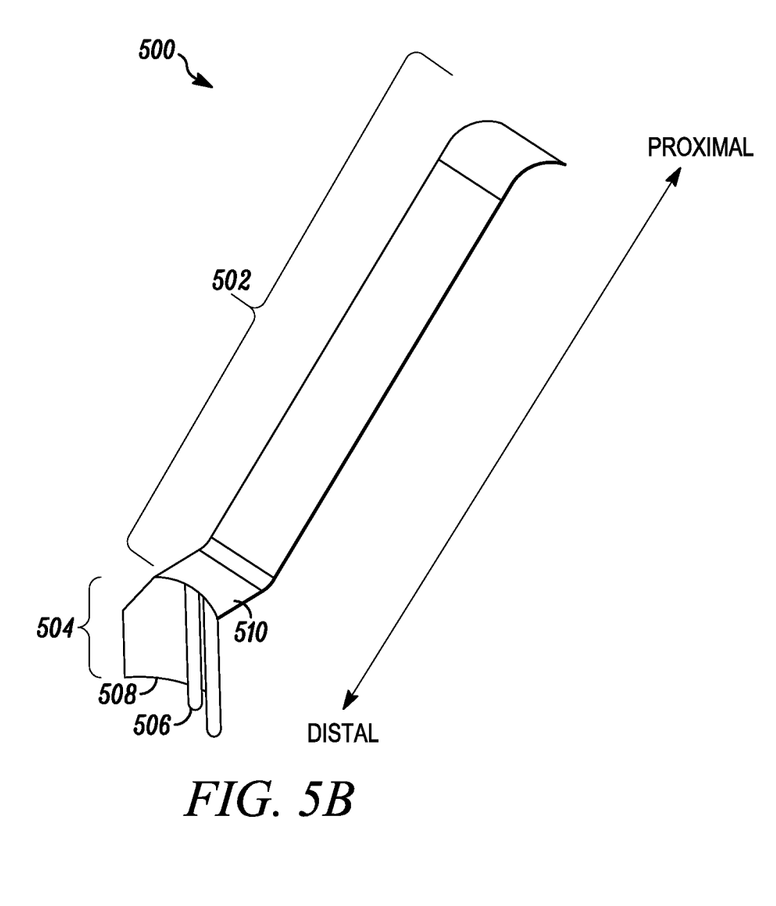

FIGS. 5a and 5b illustrate additional perspective views of a posterior retractor design, according to some embodiments. In these embodiments, the posterior retractor 500 has a handle section 502, a retraction section 504, and an anchoring element 506, each having a proximal region and a distal region. Again, an arrow in the figures illustrates the meaning of "proximal" relative to "distal." The proximal region of the retraction section 504 joins the distal region of the handle section 502, and the proximal region of the anchoring element 506 joins the distal region of the retraction section 504. The distal region of the retraction section 504 has a pelvic surface 508 that contacts a subject's pelvis during use of the posterior retractor 500. The retraction section 504 can comprise a one-piece, rigid, semi-cylindrical shape having (i) a diameter of curvature measured through the central axis 505 of the retraction section 504 that ranges from about 20 mm to about 90 mm and is at least substantially complementary to an acetabulum, and (ii) an arc ranging from about 45° to about 180°, wherein the diameter of curvature and arc are outlined in dotted lines. The retraction section 504 can have a concave surface 515 facing away from the handle section 502 and a convex surface 520 facing toward the handle section 502.

The phrase "substantially complementary to an acetabulum" can, in some embodiments, refer to a shape that substantially conforms to a portion of the perimeter of the acetabulum. In many embodiments, the complementary shape substantially circumscribes a rounded portion of the acetabulum. The complementary shape can have a arc ranging from about 10° to about 225°, from about 20° to about 200°, from about 30° to about 180°, from about 35° to about 180°, from about 40° to about 150°, from about 45° to about 90°, from about 45° to about 120°, from about 45° to about 180°, or any range therein. The complementary shape can have a diameter of curvature ranging from about 20 mm to about 90 mm, from about 25 mm to about 80 mm, from about 30 mm to about 70 mm, from about 40 mm to about 65 mm, from about 45 mm to about 60 mm, from about 50 mm to about 65 mm, or any range therein. The "arc" refers to the segment of an imaginary circle that is circumscribed by the complementary shape, and the size of the segment is defined by the angle covered from one end of the segment to the other end of the segment, wherein the angle is measured from a fulcrum point that is positioned at the central axis of the imaginary circle. The "diameter of curvature" is the diameter of the imaginary circle. The arc and diameter of curvature can be seen from the dotted lines provided in FIG. 5a.

In these embodiments, the anchoring element 506 can extend substantially normal to the pelvic surface 508 of the retraction section 504, is fashioned for penetration of an ischial bone, and can function to anchor the retraction section 504 of the posterior retractor 500 to the subject's pelvis during use of the posterior retractor 500 in the hip arthroplasty procedure.

In some embodiments, the distal region of the handle section 502 can have an impact surface 510 for receiving a pressure that forces the anchoring element 506 to penetrate the ischial bone. In some embodiments, such a force can be applied, for example, using a surgical mallet.

In some embodiments, the distal region of the handle section 502 can have a central axis that is normal to the central axis of the retraction section 504, of which neither central axis is on the horizontal plane, and can form an angle with the mid-region of the handle section 502 such that the central axis of the mid-region can be at an angle ranging from about 30° to about 60° to the central axis of the retraction section 504. In some embodiments, the central axis of the mid-region is at an angle of 45° to the central axis of the retraction section 504. FIG. 4 makes reference to such axes and planes. In some embodiments, the proximal region of the handle section 502 is ergonomically curved away from the horizontal plane and can curve away in a direction that at least partially opposes the direction in which the concave surface 515 of the retraction section 504 faces. In some embodiments, the ergonomic shape can comprise any rounded shape, such as a knob, sphere, cylinder, dished shape, conical shape, and the like.

In some embodiments, the handle section ranges in length from about 6 inches to about 12 inches. And, in some embodiments, the distance from the distal region of the handle section to the pelvic surface of the retraction section ranges from about 1 inch to about 3 inches. In some embodiments, the anchoring element ranges from about 0.25 inches to about 0.75 inches in length from the pelvic surface of the retraction section to the tip of the anchoring element.

In some embodiments, the pelvic surface of the posterior retractor can be flat, rounded, blunt, sharp, serrated, or otherwise shaped or textured to provide a desired function, such as a surface that provides extra stability following anchoring of the anchoring element into the ischial bone or, perhaps, to provide a surface that is less disruptive of the surface of the ischial bone.

The posterior retractor can comprise any FDA approved material that would meet the performance requirements of the instrument, such that the instrument has a sufficient hardness and modulus of elasticity to perform the function of a posterior retractor. In some embodiments, for example, the posterior retractor can comprise an aluminum or aluminum alloy, a polymeric material, a ceramic material, or a surgical grade iron alloy. In some embodiments, the surgical grade alloy can have from about 12% to about 20% chromium, from about 0.2% to about 3% molybdenum, from about 8% to about 12% nickel and from about 0.08% to about 0.25% carbon. In some embodiments, the retractor can be fashioned from the surgical grade iron alloy as a single-piece instrument. In some embodiments, wear items, such as the anchoring element, can be replaced. In some embodiments, the anchoring item can be smooth, threaded, serrated, barbed, or otherwise textured, such that the texturing can assist in provided a stable anchor during arthroplasty.

In some embodiments, the central axes of the handle section, the retraction section, and the anchoring element can all lie on the vertical plane. Moreover, in some embodiments, the retractor can have a shape that useful in the arthroplastic procedures of both the right hip and the left hip of the subject. Referring back to FIGS. 3a and 3b, the current state-of-the-art retractors shown in FIG. 3a require different designs for use with right and left hips, as shown by retractors 300, whereas the improved retractor shown in FIG. 3b can be used on either the right or the left hip during an arthroplasty.

The teachings also include posterior retractor embodiments, wherein the retractor comprises a handle section; and a retraction section comprising an anchoring element; wherein, the handle section, the retraction section, and the anchoring element each have a central axis and are positioned relative to a horizontal plane. The handle section can comprise a proximal region, a mid-region, and a distal region, wherein the mid-region can be on the horizontal plane, and the central axis of the mid-region can be at an angle ranging from about 35° to about 50° to the central axis of the retraction section, which may not be on the horizontal plane. Accordingly, the central axes of the handle section and retraction section can be on different planes, parallel or intersecting planes, to allow for some reconfiguration of the improved retractor for a variety of special applications.

In some embodiments, the handle section can have a length ranging from about 7 inches to about 9 inches, a width that is equal along the length of the handle section ranging from about 0.75 inches to about 2.0 inches, and a thickness that is 0.05 inches to about 0.25 inches. And, in these embodiments, the proximal region of the handle section can be ergonomically curved away from the horizontal plane and in the direction of the anchoring element.

In these embodiments, the retraction section can have a proximal region and a distal region, wherein the proximal region of the retraction section joins the distal region of the handle. And, the distal region of the retraction section can have a pelvic surface that contacts a subject's pelvis during use of the posterior retractor. The retraction section can comprise a one-piece, rigid, semi-cylindrical shape having (i) a diameter of curvature that ranges from about 20 mm to about 90 mm and is at least substantially complementary to an acetabulum, and (ii) an arc ranging from about 45° to about 180°. The retraction section can also have a concave surface facing away from the handle section and a convex surface facing toward the handle section.

In these embodiments, the distance from the distal region of the handle section to the pelvic surface of the retraction section can range from about 1 inch to about 2 inches, from about 0.50 inches to about 2.5 inches, from about 0.75 inches to about 2.25 inches, from about 1.0 inch to about 1.5 inches, or any range therein. In some embodiments, the thickness of the retraction section ranges from about 0.05 inches to about 0.25 inches, from about 0.07 inches to about 0.50 inches, from about 0.10 inches to about 0.20 inches, or any range therein.

In some embodiments, the distal region of the handle section can have an impact surface for receiving a pressure that forces the anchoring element to penetrate an ischial bone. The impact surface can range in length, measured proximal to distal, from about 0.50 inches to about 3.0 inches, from about 0.75 inches to about 2.50 inches, from about 1.0 inch to about 2.0 inches, or any range therein. In some embodiments, the thickness of the impact surface is greater than the thickness of the handle section.

In many embodiments, the anchoring element extends at least substantially normal to the pelvic surface of the retraction section, is fashioned for penetration of the ischial bone, ranges from about 0.25 inches to about 0.75 inches in length from the pelvic surface of the retraction section to the tip of the anchoring element, and functions to anchor the retraction section of the posterior retractor to the subject's pelvis during use of the posterior retractor in the hip arthroplasty procedure. In some embodiments, the length of the anchoring element ranges from about 0.10 inches to about 0.90 inches, from about 0.20 inches to about 0.8 inches, from about 0.30 inches to about 0.7 inches, from about 0.40 inches to about 0.60 inches, from about 0.10 inches to about 0.50 inches, from about 0.10 inches to about 0.40 inches, from about 0.15 inches to about 0.25 inches, or any range therein. In some embodiments, the improved retractor can have a plurality of anchoring elements, such as 1, 2, 3, 4, 5, or more anchoring elements. The lengths of each of the plurality of anchoring elements can be independently selected, such that the lengths of each of the plurality of anchoring elements can be the same, different, in a desired pattern, or the combination thereof, in order to provide the anchoring performance desired by the posterior retractor.

In some embodiments, the retractor can be fashioned as a single-piece instrument from a surgical grade iron alloy comprising from about 12% to about 20% chromium, from about 0.2% to about 3% molybdenum, from about 8% to about 12% nickel and from about 0.08% to about 0.25% carbon. In some embodiments, the central axes of the handle section, the retraction section, and the anchoring element can all lie at least substantially on the same vertical plane; and, in some embodiments, the retractor can have a shape that is useful in arthroplastic procedures of both the right hip and the left hip of the subject;

In some embodiments, the teachings provide a posterior retractor, comprising a handle section having a means for (i) applying leverage to a retraction section and (ii) retracting soft tissue around a hip joint during an arthroplastic procedure. In these embodiments, the retraction section comprises a means for anchoring the posterior retractor a pelvic surface of a subject having the arthroplastic procedure. And, in these embodiments, the posterior retractor can comprise a surgical grade iron alloy comprising from about 12% to about 20% chromium, from about 0.2% to about 3% molybdenum, from about 8% to about 12% nickel and from about 0.08% to about 0.25% carbon. In some embodiments, the retractor can be fashioned from the surgical grade iron alloy as a single-piece instrument.

Figure 6:
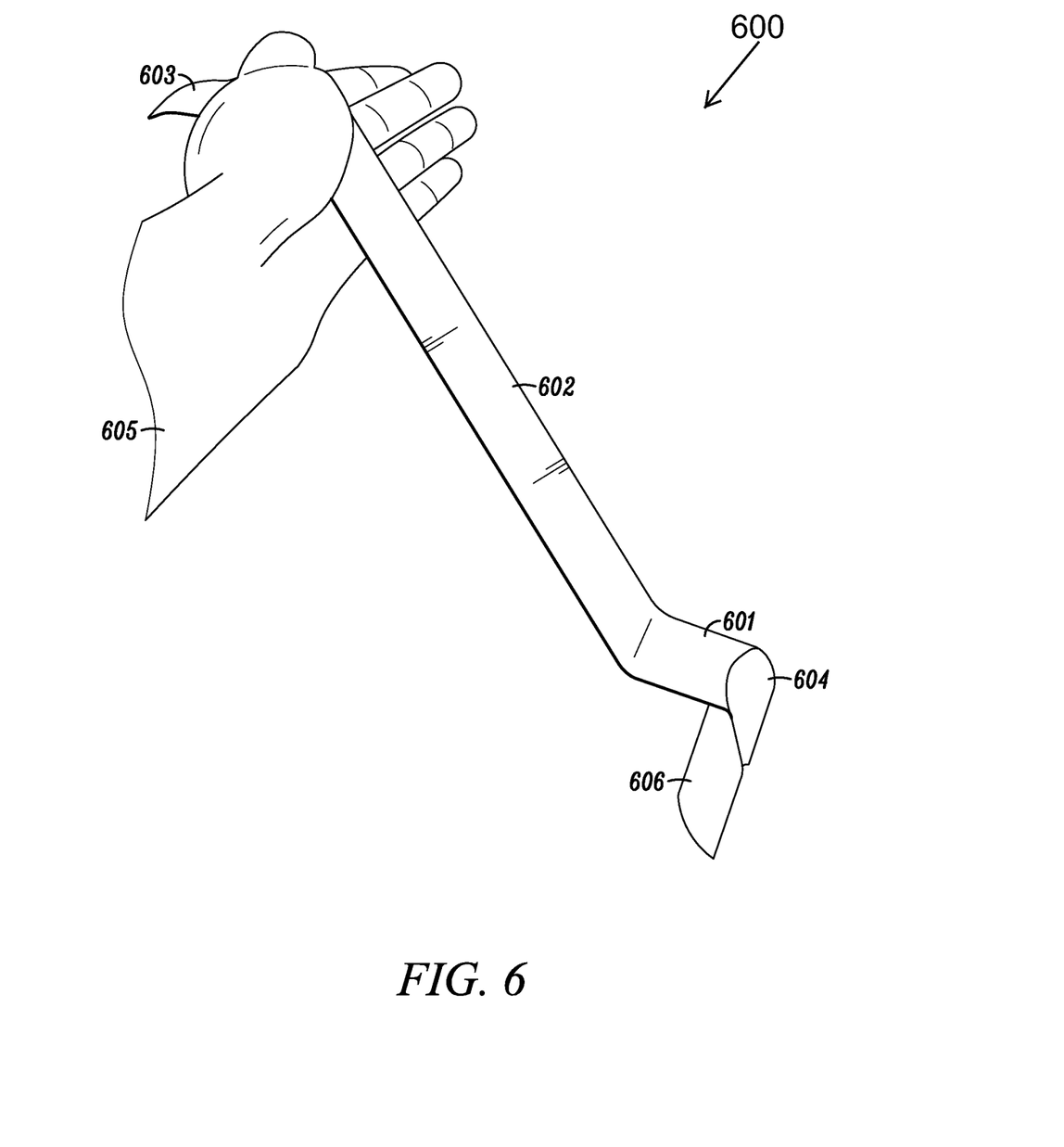
FIG. 6 illustrates a view of a single-piece posterior retractor held in an adult human hand, according to some embodiments.

FIG. 6 illustrates a view of a single-piece posterior retractor held in an adult human hand, according to some embodiments. Posterior retractor 600 is held in human hand 605 to show a size that may be desirable for retracting soft tissue during a hip arthroplasty of a subject. The handle section 602 has an ergonomic curve 603 for comfort, as well as an impact surface 601 for applying force to the retraction section 604 and driving the anchoring element 606 into the ischial bone of the subject.

The posterior retractor can be manufactured using any method known to one of skill in the art of manufacturing. For example, the retractor can be a casting in some embodiments or, it can be cut from a billet. In some embodiments, parts of the retractor can be separately cast, cut, or a combination thereof, and then later assembled. In some embodiments, the parts of the retractor can be permanently attached or removably attached to one another. In some embodiments, the retractor can be formed as a single piece or, perhaps, a single piece having a replacement part, such as the anchoring element.

The teachings provided herein also include a method of implanting an acetabular prosthesis. The method comprises incising soft tissue over a hip joint comprising an acetabulum having a socket, and a femoral head. Any retractor taught herein is positioned posterior to the acetabulum such that the anchoring element is placed substantially normal to an ischial bone surface, and the concave surface of the retraction element is placed substantially complementary to the acetabulum. The anchoring element is forced into the ischial bone to anchor the retraction section to the ischial bone, and the soft tissue is retracted with the retracting section. The socket of the acetabulum is reamed to prepare the socket for insertion of an acetabular prosthesis; and, the acetabular prosthesis is positioned in the acetabulum. One of skill will appreciate that there are variations in the manner in which the posterior retractor can be used and that these variations are contemplated.

Figure 7:
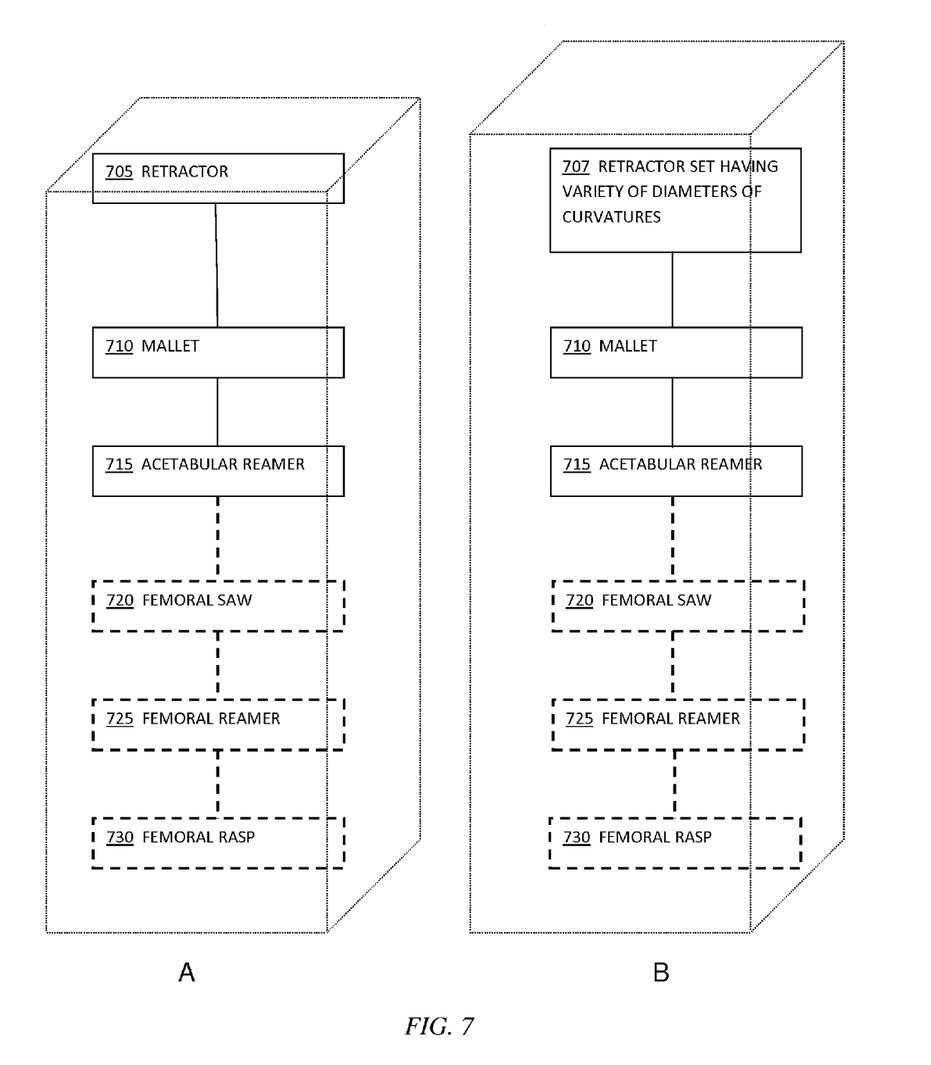
FIG. 7 illustrates the kits taught herein, according to some embodiments.

The teachings provided herein also include a kit comprising any of the retractors taught herein, a mallet 710 for applying force to the anchoring element of the retractor 705; and, an acetabular reamer 715 to prepare the socket of an acetabulum for insertion of an acetabular prosthesis. In some embodiments, the kits further comprise a femoral saw 720, a femoral reamer 725, and a femoral rasp 730. In some embodiments, the kits further comprise a set 707 of acetabular reamers of a variety of sizes to prepare the socket of an acetabulum for insertion of an acetabular prosthesis. FIG. 7 illustrates the kits taught herein, according to some embodiments.

While particular embodiments of the present invention have been shown and described, one of skill will appreciate that all possible variations of the general concept could not be provided. A numerous variety of shapes, sizes, and materials have been contemplated. Accordingly, changes and modifications can be made to the teachings herein, within the knowledge of one of skill, without departing from the invention in its broader aspects. Moreover, many of the embodiments can be used together, or in a combination, to fulfill the purpose and nature of the invention.

We claim:

1. A posterior retractor comprising a handle section; and a one-piece, rigid retraction section comprising a single, rigid anchoring element with a single, bone-penetrating tip; wherein, the rigid retraction section and the rigid anchoring element each have a central axis and are positioned relative to a horizontal plane;

the handle section comprises a proximal region, a mid-region, and a distal region, wherein the mid-region is on the horizontal plane, and the central axis of the mid-region is at an angle ranging from about 35° to about 50° to the central axis of the rigid retraction section which is not on the horizontal plane; the handle section has a length ranging from about 7 inches to about 9 inches, a width that is equal along the length of the handle section ranging from about 0.75 inches to about 2.0 inches, and a thickness that is 0.05 inches to about 0.25 inches; and the proximal region of the handle section is ergonomically curved away from the horizontal plane and in the direction of the rigid anchoring element;

the one-piece, rigid retraction section has a proximal region and a distal region, wherein the proximal region of the rigid retraction section joins the distal region of the handle, and the distal region of the rigid retraction section has a pelvic surface that contacts a subject's pelvis during use of the posterior retractor; the rigid retraction section comprising a one-piece, rigid, semi-cylindrical shape having (i) a diameter of curvature that ranges from about 20 mm to about 90 mm and is at least substantially complementary to an acetabulum, and (ii) an arc ranging from about 45° to about 180°; the rigid retraction section having a concave surface facing away from the handle section and a convex surface facing toward the handle section; and, wherein the distance from the distal region of the handle section to the pelvic surface of the rigid retraction section ranges from about 1 inch to about 2 inches, and the thickness of the rigid retraction section ranges from about 0.05 inches to about 0.25 inches; wherein, the distal region of the handle section has an impact surface for receiving a pressure that forces the rigid anchoring element to penetrate an ischial bone;

the single, rigid anchoring element with the single, bone-penetrating tip extends at least substantially normal to the pelvic surface of the rigid retraction section, is fashioned for penetration of the ischial bone, ranges from about 0.25 inches to about 0.75 inches in length from the pelvic surface of the rigid retraction section to the single, bone-penetrating tip of the single, rigid anchoring element, and functions to anchor the rigid retraction section of the posterior retractor to the subject's pelvis during use of the posterior retractor in the hip arthroplasty procedure;

the retractor is fashioned as a single-piece instrument from a surgical grade iron alloy comprising from about 12% to about 20% chromium, from about 0.2% to about 3% molybdenum, from about 8% to about 12% nickel and from about 0.08% to about 0.25% carbon;

the central axes of the handle section, the rigid retraction section, and the single, rigid anchoring element with the single, bone-penetrating tip all lie at least substantially on the vertical plane, wherein the vertical plane is at least substantially normal to the horizontal plane; and, the retractor has a shape that useful in the arthroplastic procedures of both the right hip and the left hip of the subject.

2. The retractor of claim 1, wherein the distal region of the handle has a central axis that is normal to the central axis of the rigid retraction section, of which neither central axis is on the horizontal plane, and forms an angle with the mid-region of the handle section such that the central axis of the mid-region is at an angle ranging from about 30° to about 60° to the central axis of the rigid retraction section, wherein the single, rigid anchoring element is permanently attached to the rigid retraction section.

3. The retractor of claim 1, wherein the proximal region of the handle section is ergonomically curved away from the horizontal plane in a direction that opposes the direction in which the concave surface of the rigid retraction section faces, and the entire posterior retractor is fashioned as a single-piece instrument.

4. The retractor of claim 1, wherein the retraction section has a plurality of rigid anchoring elements.

5. The retractor of claim 1, wherein the pelvic surface is flat and smooth.

6. The retractor of claim 1, wherein the central axes of the handle section, the rigid retraction section, and the anchoring element all lie at least substantially on the vertical plane, and the single, rigid anchoring element is removably attached to the retractor and has a textured surface selected from the group consisting of a barbed surface, a serrated surface, or a threaded surface.

7. A method of implanting an acetabular prosthesis, comprising:

incising soft tissue over a hip joint comprising an acetabulum having a socket, and a femoral head;

positioning the retractor of claim 1 posterior to the acetabulum such that the single, rigid anchoring element with the single, bone-penetrating tip is placed at least substantially normal to an ischial bone surface, and the concave surface of the rigid retraction section is placed at least substantially complementary to the acetabulum;

forcing the single, rigid anchoring element into the ischial bone to anchor the rigid retraction section to the ischial bone;

retracting the soft tissue with the rigid retraction section;

reaming the socket of the acetabulum to prepare the socket for insertion of an acetabular prosthesis; and, positioning the acetabular prosthesis in the acetabulum.

8. A kit comprising:

the retractor of claim 1;

a mallet for applying force to the single, rigid anchoring element of the retractor; and, an acetabular reamer to prepare the socket of an acetabulum for insertion of an acetabular prosthesis.

9. The kit of claim 8 further comprising a femoral saw, a femoral reamer, and a femoral rasp.

10. A kit comprising:

A set of retractors, each being a retractor of claim 1, wherein the set provides a variety of diameters of curvature ranging from about 45 mm to about 85 mm, and each retractor section has an arc in the range of from about 45° to about 180°;

a mallet for applying force to the single, rigid anchoring element of each the retractors; and, a set of acetabular reamers of a variety of sizes to prepare the socket of an acetabulum for insertion of an acetabular prosthesis.

11. The kit of claim 10 further comprising a femoral saw, a femoral reamer, a rigid anchoring element replacement, and a femoral rasp.

12. A posterior retractor comprising a handle section; and a one-piece, rigid retraction section having a plurality of rigid anchoring elements, each having a bone-penetrating tip; wherein, the retraction section, and the plurality of rigid anchoring elements each have a central axis and are positioned relative to a horizontal plane;

the handle section comprises a proximal region, a mid-region, and a distal region, wherein the mid-region is on the horizontal plane, and the central axis of the mid-region is at an angle ranging from about 35° to about 50° to the central axis of the rigid retraction section which is not on the horizontal plane; the handle section has a length ranging from about 7 inches to about 9 inches, a width that is equal along the length of the handle section ranging from about 0.75 inches to about 2.0 inches, and a thickness that is 0.05 inches to about 0.25 inches; and the proximal region of the handle section is ergonomically curved away from the horizontal plane and in the direction of the rigid anchoring element;

the one-piece, rigid retraction section has a proximal region and a distal region, wherein the proximal region of the rigid retraction section joins the distal region of the handle, and the distal region of the rigid retraction section has a pelvic surface that contacts a subject's pelvis during use of the posterior retractor; the rigid retraction section comprising a one-piece, rigid, semi-cylindrical shape having (i) a diameter of curvature that ranges from about 20 mm to about 90 mm and is at least substantially complementary to an acetabulum, and (ii) an arc ranging from about 45° to about 180°; the rigid retraction section having a concave surface facing away from the handle section and a convex surface facing toward the handle section; and, wherein the distance from the distal region of the handle section to the pelvic surface of the rigid retraction section ranges from about 1 inch to about 2 inches, and the thickness of the rigid retraction section ranges from about 0.05 inches to about 0.25 inches; wherein, the distal region of the handle section has an impact surface for receiving a pressure that forces the rigid anchoring element to penetrate an ischial bone;

each of the plurality of anchoring elements extends at least substantially normal to the pelvic surface of the rigid retraction section, is fashioned for penetration of the ischial bone, ranges from about 0.25 inches to about 0.75 inches in length from the pelvic surface of the rigid retraction section to the single, bone-penetrating tip of the single, rigid anchoring element, and functions to anchor the rigid retraction section of the posterior retractor to the subject's pelvis during use of the posterior retractor in the hip arthroplasty procedure;

the retractor is fashioned as a single-piece instrument from a surgical grade iron alloy comprising from about 12% to about 20% chromium, from about 0.2% to about 3% molybdenum, from about 8% to about 12% nickel and from about 0.08% to about 0.25% carbon; and, the central axes of the handle section and the rigid retraction section lie at least substantially on the vertical plane, wherein the vertical plane is at least substantially normal to the horizontal plane.

13. A kit comprising:

the retractor of claim 12;

a mallet for applying force to the plurality of rigid anchoring elements of the retractor; and, an acetabular reamer to prepare the socket of an acetabulum for insertion of an acetabular prosthesis.

14. The kit of claim 13 further comprising a femoral saw, a femoral reamer, and a femoral rasp.

15. A method of implanting an acetabular prosthesis, comprising:

incising soft tissue over a hip joint comprising an acetabulum having a socket, and a femoral head;

positioning the retractor of claim 12 posterior to the acetabulum such that the plurality of rigid anchoring elements are placed at least substantially normal to an ischial bone surface, and the concave surface of the rigid retraction section is placed at least substantially complementary to the acetabulum;

forcing the plurality of rigid anchoring elements into the ischial bone to anchor the rigid retraction section to the ischial bone;

retracting the soft tissue with the rigid retraction section;

reaming the socket of the acetabulum to prepare the socket for insertion of an acetabular prosthesis; and, positioning the acetabular prosthesis in the acetabulum.

* * * * *